US009815695B2

(12) United States Patent
Cummings et al.

(10) Patent No.: US 9,815,695 B2
(45) Date of Patent: Nov. 14, 2017

(54) IN SITU RESTORATION OF APATITE-BASED CHROMATOGRAPHY RESINS

(71) Applicant: Bio-Rad Laboratories, Inc., Hercules, CA (US)

(72) Inventors: Larry J. Cummings, Pleasant Hill, CA (US); Jie He, South San Francisco, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 176 days.

(21) Appl. No.: 13/891,502

(22) Filed: May 10, 2013

(65) Prior Publication Data

US 2013/0323812 A1 Dec. 5, 2013

Related U.S. Application Data

(60) Provisional application No. 61/653,172, filed on May 30, 2012.

(51) Int. Cl.
| | |
|---|---|
| *C01B 25/32* | (2006.01) |
| *C01B 25/455* | (2006.01) |
| *B01D 15/20* | (2006.01) |
| *C07K 1/18* | (2006.01) |
| *B01J 20/04* | (2006.01) |
| *B01J 20/282* | (2006.01) |
| *B01J 20/34* | (2006.01) |
| *C07K 1/20* | (2006.01) |
| *C07K 1/22* | (2006.01) |

(52) U.S. Cl.
CPC .......... *C01B 25/327* (2013.01); *B01D 15/203* (2013.01); *B01J 20/048* (2013.01); *B01J 20/282* (2013.01); *B01J 20/3433* (2013.01); *B01J 20/3475* (2013.01); *C01B 25/455* (2013.01); *C07K 1/18* (2013.01); *C07K 1/20* (2013.01); *C07K 1/22* (2013.01)

(58) Field of Classification Search
None
See application file for complete search history.

(56) References Cited

U.S. PATENT DOCUMENTS

| | | | |
|---|---|---|---|
| 3,737,516 | A | 6/1973 | Jenner |
| 4,053,561 | A | 10/1977 | Irani |
| 4,859,342 | A | 8/1989 | Shirasawa et al. |
| 5,332,503 | A | 7/1994 | Lee et al. |
| 5,744,587 | A | 4/1998 | Alaska et al. |
| 5,783,217 | A | 7/1998 | Lee et al. |
| 6,156,178 | A | 12/2000 | Mansfield et al. |
| 6,602,697 | B1 | 8/2003 | Cook, III |
| 7,476,722 | B2 | 1/2009 | Vedantham et al. |
| 7,659,373 | B2 | 2/2010 | Burg et al. |
| 8,058,407 | B2 | 11/2011 | Sun et al. |
| 8,067,182 | B2 | 11/2011 | Kelley et al. |
| 2003/0166869 | A1 | 9/2003 | Vedantham et al. |
| 2004/0254267 | A1* | 12/2004 | Nagae ........................... 523/333 |
| 2004/0265298 | A1 | 12/2004 | Lin |
| 2005/0107594 | A1 | 5/2005 | Sun et al. |
| 2005/0209100 | A1 | 9/2005 | Duval et al. |
| 2006/0246544 | A1 | 11/2006 | Kang et al. |
| 2007/0060741 | A1* | 3/2007 | Kelley et al. .............. 530/387.1 |
| 2009/0047723 | A1 | 2/2009 | Jensen et al. |
| 2009/0186396 | A1 | 7/2009 | Gagnon |
| 2009/0187005 | A1 | 7/2009 | Gagnon |
| 2009/0264651 | A1 | 10/2009 | Daly |
| 2009/0318674 | A1 | 12/2009 | Gagnon |
| 2010/0113751 | A1 | 5/2010 | Sun et al. |
| 2010/0291059 | A1 | 11/2010 | Sakuraba et al. |
| 2011/0178276 | A1 | 7/2011 | Cummings et al. |
| 2012/0149636 | A1 | 6/2012 | Kraynov et al. |
| 2012/0192901 | A1 | 8/2012 | Cummings |
| 2012/0202975 | A1 | 8/2012 | Cummings et al. |

FOREIGN PATENT DOCUMENTS

| | | | |
|---|---|---|---|
| EP | 0 256 836 | A1 | 2/1988 |
| EP | 1 081 221 | A1 | 3/2001 |
| EP | 2138505 | B1 | 8/2014 |
| JP | 2001-525338 | A | 12/2001 |
| JP | 2010-501623 | A | 1/2010 |
| WO | WO 03/059935 | A2 | 7/2003 |
| WO | WO 2006/099308 | A2 | 9/2006 |
| WO | 2008/025748 | A1 | 3/2008 |
| WO | 2008/113011 | A2 | 9/2008 |
| WO | 2008/143354 | A1 | 11/2008 |
| WO | WO 2009/017491 | A1 | 2/2009 |
| WO | 2010/034442 | A1 | 4/2010 |
| WO | 2010/148143 | A1 | 12/2010 |

OTHER PUBLICATIONS

CFT Ceramic Fluoroapatite. Instruction Manual. Bio-Rad Laboratories, Inc. Jan. 9, 2012 (date obtained from WayBackMachine).*
Notice of Allowance dated Oct. 1, 2014 for U.S. Appl. No. 13/006,022, 14 pages.
International Search Report and Written Opinion from PCT/US2012/023512, dated May 10, 2012.
The International Search Report from PCT/US2011/021158, dated Mar. 17, 2011.
The International Search Report from PCT/US2011/048082, dated Mar. 20, 2012.
U.S. Appl. No. 13/006,022, filed Jan. 13, 2011 (25 pages).
U.S. Appl. No. 13/205,354, filed Aug. 8, 2011 (26 pages).
U.S. Appl. No. 13/363,670, filed Feb. 1, 2012 (14 pages).
Gorbunoff et al.; "The interaction of proteins with hydroxyapatite—I. Role of protein charge and structure"; 1984, *Analytical Biochemistry*, vol. 136, No. 2, pp. 425-432.
Office Action from U.S. Appl. No. 13/006,022, dated Jun. 29, 2012.

(Continued)

*Primary Examiner* — Katherine Zalasky
*Assistant Examiner* — Kara Graber
(74) *Attorney, Agent, or Firm* — Kilpatrick Townsend & Stockton LLP

(57) ABSTRACT

Methods and compositions are provided for treatment of an apatite-based resin from which retained solutes have been eluted by an elution buffer that contains an alkali metal salt with solutions of calcium ion, phosphate ion, and hydroxide separately from any sample loading and elution buffers. The treatment solutions restore the resin, reversing the deterioration that is caused by the alkali metal salt in the elution buffer.

25 Claims, No Drawings

(56) References Cited

OTHER PUBLICATIONS

Office Action from U.S. Appl. No. 13/006,022, dated Nov. 15, 2012.
Office Action from U.S. Appl. No. 13/363,670, dated Mar. 11, 2013.
Office Action from U.S. Appl. No. 13/363,670, dated Sep. 21, 2012.
Britsch, "Purification of Flavanone 3 beta-Hydroxylase from *Petunia hybrida*: Antibody preparation and Characterization of a Chemogenetically Defined Mutant", *Archives of Biochemistry and Biophysics*, 276(2):348-354 (1990).
Extended European Search Report dated Jul. 18, 2014 for EP Application No. 12742721.9, 6 pages.
Extended European Search Report dated Jul. 21, 2014 for EP Application No. 11733384.9, 7 pages.
Office Action from U.S. Appl. No. 13/205,354, dated Feb. 6, 2014, 8 pages.
Office Action from U.S. Appl. No. 13/363,670, dated Nov. 15, 2013.
International Search Report from PCT/US2013/40591, dated Oct. 8, 2013.
Office Action from U.S. Appl. No. 13/363,670, dated Jul. 2, 2013.
Notice of Reasons for Rejection dated May 11, 2015 for Japanese Patent Application No. 2013-524960, with English Translation.
Bankston et al. "pH Transients in hydroxyapatite chromatography columns—Experimental evidence and phenomenological modeling", Journal of Chromatography A, 1217 (2010) 2123-2131.
Extended European Search Report dated Dec. 17, 2015 for EP Application No. 13796784.0.
International Search Report and Written Opinion from PCT/US2015/037112, dated Sep. 29, 2015.
International Search Report and Written Opinion from PCT/US2015/037116, dated Sep. 16, 2015, 12 pages.
International Search Report and Written Opinion from PCT/US2015/037145, dated Oct. 6, 2015.
U.S. Appl. No. 14/598,719, filed Jan. 16, 2015 (32 pages).
U.S. Appl. No. 14/932,080, filed Nov. 4, 2015 (xx pages).
U.S. Appl. No. 14/747,181, filed Jun. 23, 2015 (xx pages).
U.S. Appl. No. 14/747,221, filed Jun. 23, 2015 (xx pages).
U.S. Appl. No. 14/747,162, filed Jun. 23, 2015 (xx pages).
Extended European Search Report dated Dec. 17, 2014 for EP Application No. 11818724.4, 7 pages.
CHT Ceramic Hydroxyapatite: Instruction Manual, 16 pages (2001) http://www.bio-rad.com/cmc_upload/0/000/039/227/Lit-611d.pdf.
Schroder et al., "Hydroxyapatite chromatography: altering the phosphate-dependent elution profile of protein as a function of pH", *Analytical Biochemistry*, vol. 313, pp. 176-178 (2003).
Larsen et al., "Solubility Study of the Initial Formation of Calcium Orthophosphates from Aqueous Solutions at pH5-10", *Arch oral Biol.*, vol. 31, No. 9, pp. 565-572 (1986).
Recillas et al., "Studies on the precipitation behavior of calcium phosphate solutions", Journal of Ceramic Processing Research, vol. 13, No. 1, pp. 5-10 (2012).
Notice of Allowance dated Jul. 25, 2014 for U.S. Appl. No. 13/205,354, 9 pages.

\* cited by examiner

IN SITU RESTORATION OF APATITE-BASED CHROMATOGRAPHY RESINS

CROSS-REFERENCE TO RELATED PATENT APPLICATIONS

The present patent application claims benefit of priority to U.S. Provisional Patent Application No. 61/653,172, filed May 30, 2012, which is incorporated by reference for all purposes.

BACKGROUND OF THE INVENTION

1. Field of the Invention

This invention relates to apatite-based chromatographic resins and their use in the purification of proteins and other target molecules from biological samples.

2. Description of the Prior Art

Apatite in its various forms, examples of which are hydroxyapatite, ceramic hydroxyapatite, fluoroapatite, and fluoride-enhanced apatite, is used as a chromatographic solid phase in the separation and purification of a wide variety of target molecules by way of binding mechanisms that involve either affinity, ion exchange or hydrophobic interactions, or combinations of these mechanisms. Apatite-based chromatography resins are particularly useful in protein purifications, notably purifications of recombinant proteins from host cell proteins, aggregates, endotoxin, and DNA. Sample loading of an apatite-based resin, particularly with proteins, is most often conducted by first equilibrating the resin to pH 6.5 with phosphate buffer at 2 mM to 5 mM, and then loading the sample in a solution at the same pH and buffer content. Once the sample is loaded, unbound components are washed from the resin and the target molecule is eluted with an elution buffer that typically contains an alkali metal salt, most often at pH of 8.0 or below. The equilibration and loading buffers both saturate the hydroxyapatite surface with hydroxonium ions ($H_3O^+$), which are then desorbed upon exposure to the elution buffer. This desorption causes the resin to deteriorate over time, resulting in a loss of resin mass and a decline in the particle strength of the resin. Of potential relevance to this issue is the disclosure of commonly owned, co-pending U.S. patent application Ser. No. 13/205,354, filed Aug. 8, 2011, entitled "Elution of Proteins From Hydroxyapatite Resins Without Resin Deterioration," inventor L. J. Cummings. That disclosure describes the use of elution buffers that include calcium ions and phosphate ions at a pH of 6.0 or below, thereby both eluting the protein and treating the resin with these ions at the same time. While this buffer is effective in inhibiting the resin deterioration that occurs without the inclusion of the calcium ions in the buffer, the exposure of the resin to the calcium ions in this method is limited to the duration of the elution step and the volume of the elution buffer, and the product eluate, although lacking the impurities in the original sample, contains calcium ions.

SUMMARY OF THE INVENTION

It has now been discovered that the deterioration of an apatite-based resin during a chromatographic procedure for purifying a target molecule from a sample can be reversed by a post-elution treatment of the resin with a succession of treatment solutions that contain calcium ion, phosphate ion, and hydroxide ion, by applying these solutions separately from the sample purification steps such as column equilibration, sample loading, and elution. The calcium ion, phosphate ion, and hydroxide ion are referred to herein as restoration materials. The treatment solutions containing these ions thus do not interfere with the equilibration, loading, and elution buffers, and the ions themselves, referred to herein as "restoration materials," are not transferred from these treatment solutions to the solution of purified target molecule, i.e., the product solution. In certain cases, phosphate ion may be included in the equilibration, loading, and elution solutions as part of the buffers in these solutions, and will thus be retained from these solutions in the purified product. It is demonstrated herein, however, that resin restoration, whether partial or complete, can thus be performed separately from product purification, by simply applying the restoration materials as additional steps in a protocol consisting of a series of solutions passed through the resin. In certain implementations of the invention, a single resin is used for multiple purifications, i.e., purifications of target molecules from multiple samples, in succession, with each sample being followed by treatment of the resin with the three restoration ions which are then cleared from the resin, or at least the calcium ion is cleared, before loading the succeeding sample. Sample purification can thus be alternated with column restoration by simply exchanging the solution being passed through the column while obtaining the purified protein separate from, i.e., in a solution that is devoid of, the restoration materials.

These and other objects, features, embodiments, and advantages of the invention will be apparent from the description that follows.

DETAILED DESCRIPTION OF SELECTED EMBODIMENTS

In some embodiments, post-elution treatment of apatite resin with a treatment solution containing calcium ion, a treatment solution containing phosphate ion, and a treatment solution containing hydroxide ion, can restore the apatite resin. The use of one or more of these treatment solutions to restore apatite resin can be performed after steps of equilibration, loading, washing, and elution have been performed as described herein.

Calcium ion for use as a restoration material in the procedures described herein can be supplied by any soluble calcium salt, typically a salt that is soluble in water, or by calcium hydroxide. Calcium halides and calcium nitrate are examples of calcium salts that can be used, and calcium chloride is particularly convenient when the alkali metal halide in the elution buffer is an alkali metal chloride. The calcium ion concentration and the amount of the calcium ion solution passed through the resin can vary, but will generally be selected as any amount that will at least partially reverse the deterioration of the resin caused by the alkali metal halide in the elution buffer. In certain embodiments of the concepts herein, best results will be achieved with a calcium ion concentration of from about 10 ppm (0.25 mM) to about 2000 ppm (49.9 mM), and in many cases about 30 ppm (0.75 mM) to about 1000 ppm (24.95 mM), including 40 ppm, 50 ppm, 60 ppm, 70 ppm, 100 ppm, 150 ppm, 200 ppm, 250 ppm, 500 ppm, or 750 ppm. The volume of the solution needed to achieve the restoration can vary with the calcium ion concentration, but in most cases best results will be achieved with from about 1.0 to about 10.0 resin volumes of solution, and in many cases from about 1.5 to about 6 resin volumes, including 2, 3, 4, or 5 resin volumes. The calcium ion solution can simply be an aqueous solution of a calcium salt without other solutes, and the pH during treatment with this solution can be unchanged from the pH of the solution immediately preceding this solution.

Phosphate ion for use in the elution buffers can likewise be supplied from any soluble phosphate salt, typically a salt that is soluble in water. Alkali metal or alkaline earth metal phosphates are examples, with sodium phosphate as a particularly convenient example. As in the case of the calcium ion, the concentration and amount of the phosphate ion solution can vary, but will generally be selected as any amount that will at least partially reverse the resin deterioration, particularly in combination with the calcium ion treatment. Here again, the volume of the phosphate solution needed to achieve the desired degree of restoration will vary with the concentration of the phosphate ion and the degree of restoration sought to be achieved. In certain embodiments of the concept herein, best results will be achieved with a phosphate ion concentration of from about 50 mM to about 1 M, and in many cases from about 200 mM to about 750 mM, including 250 mM, 300 mM, 350 mM, 400 mM, 500 mM, 600 mM, or 700 mM. The volume for best results in many cases will be within the range of about 1.0 to about 20.0 resin volumes, and often from about 1.5 to about 10.0 resin volumes, including 2, 4, 5, 6, 7, 8, or 9 resin volumes. The pH of the phosphate ion solution will generally be about 6.5 or above, in many cases from about 6.5 to about 9.0, and often most conveniently from about 6.5 to about 7.5, including 6.6, 6.8, 7.0, 7.2, and 7.4. A phosphate buffer can thus be used for supplying the phosphate ion, and the treatment solution in many embodiments can contain the phosphate buffer, adjusted to the desired pH, and no other solutes.

A degree of resin restoration can be achieved with either the calcium ion treatment preceding the phosphate ion treatment (i.e., the calcium ion treatment directly following the application of the alkali metal halide-containing elution buffer to the resin for elution of the target molecule), or with the phosphate ion treatment preceding the calcium ion treatment. In some cases, however, a greater degree of restoration can be achieved by applying the calcium ion treatment first, followed by the phosphate ion treatment. In some cases as well, best results will be achieved when the resin is treated with a wash solution between the individual restoration ion treatments to remove any excess calcium, phosphate, or hydroxide ions. A water wash will generally suffice, and the amounts can vary widely. A typical water wash will be at least about 0.2 resin volumes, and in most cases from about 0.2 to about 1.5 or from about 0.2 to about 2 resin volumes.

Regardless of whether the calcium ion precedes or follows the phosphate ion, the hydroxide ion treatment is applied as the last treatment step of the resin restoration. Any soluble form of hydroxide ion can be used, preferably water-soluble, and alkali metal hydroxides, and in many cases sodium hydroxide, are particularly convenient. As in the cases of the calcium ion and the phosphate ion, the concentration and quantity of hydroxide ion solution can vary. The hydroxide ion can clean the resin of residual proteins and contaminants and can also serve as a first step toward equilibration of the resin to the conditions to be used for the subsequent sample loading and elution of the target molecule, or for equilibration into conditions suitable for storage. In most cases, best results will be achieved with a hydroxide ion concentration of from about 0.1 M to about 5.0 M, and in many cases from about 0.3 M to about 3.0 M, including 0.5 M, 0.75 M, 1.0 M, 1.25 M, 1.5 M, 2.0 M, or 2.5 M. Suitable volumes of hydroxide ion containing treatment solution range from about 1.0 to about 20.0 resin volumes, and in many cases from about 1.5 to about 10.0 resin volumes, including 2, 3, 4, 5, 6, 7, 8, or 9 volumes.

The term "apatite-based chromatography resin" as used herein refers to apatite, hydroxyapatite, or any derivatized form of apatite. Fluoroapatite or fluoride-enhanced apatite, for example, can be formed by the reaction of calcium phosphate with ammonium fluoride. Hydroxyapatite is a form of apatite that is available in a variety of forms. Examples are gels such as BIO-GEL® HT gel (hydroxyapatite suspended in sodium phosphate buffer), BIO-GEL® HTP gel (a dried form of BIO-GEL® HT), and DNA-grade BIO-GEL® HTP (a dried form of BIO-GEL® HT with a smaller particle size than BIO-GEL® HTP). Ceramic hydroxyapatite (CHT) is a chemically pure form of hydroxyapatite that has been sintered at high temperatures. Ceramic hydroxyapatite is spherical in shape, with particle diameters ranging from about 10 microns to about 100 microns, and is typically available at nominal diameters of 20 microns, 40 microns, and 80 microns. Ceramic hydroxyapatite is macroporous, and is available in two types: Type I, with a medium porosity and a relatively high binding capacity, and Type II, with a larger porosity and a lower binding capacity. Either porosity can be used, and the optimal porosity for any particular protein separation or purification will vary with the proteins or the composition of the source mixture. All of the apatite-based resins in this paragraph are available from BIO-RAD® Laboratories, Inc. (Hercules, California, USA). The resin can be used as a chromatographic solid phase in the form of a packed bed, and can constitute either the entire packed bed or a major portion, such as 50% or more by volume, of the packed bed. The packed bed can be retained in a vessel of any configuration, and both the purification performed in the resin and the restoration of the resin can be performed either as a batch process, a continuous process, or a hybrid batch/continuous process. Suitable vessels include columns of extended length relative to width, and suitable processes include continuous processes such as a continuous flow through a column.

Deterioration of a resin that occurs upon use can cause the resin particles to lose their strength and thus to break apart into smaller particles causing blockage in the column. The deterioration can also occur as a chemical breakdown of the apatite, causing a loss of mass which can in turn result in a loss of column volume, an increase in particle breakage, or both. All such effects can be reversed by the present invention. The reversal of deterioration that can be achieved by the practice of the present invention can result in a lower rate of resin mass loss, a lower rate of decline in particle strength, or both. In many cases, the reversal of deterioration can be accompanied by increases in resin mass, particle strength, or both.

Resin equilibration, sample loading, and elution buffers are well known in the art, and selection of the optimum buffer in each case will vary with the target molecule being purified and the type of interaction by which the target molecule binds to the resin. Of particular interest among target molecules are proteins, including acidic proteins, antibodies, and monoclonal antibodies, as well as protein fragments, and polypeptides. Much, if not most, of the resin deterioration in purifying these molecules is attributable to the presence of an alkali metal halide in the elution buffer. In cases where the interaction between the target molecule and the resin is one of cation exchange, a high concentration of alkali metal halide is included in the elution buffer, typically at about 30 mM or higher, and often in the range of about 30 mM to about 200 mM, or from about 30 mM to about 2M. In cases where the interaction is one involving the formation of a calcium coordination complex such as by chelation chemistry, an elution buffer with a lower sodium chloride concentration can be used. The pH of the elution buffer in most cases will be about 8.0 or below, and particularly from about 6.0 to about 8.0. In all cases in which the elution buffer contains an alkali metal halide, however, the present invention will be beneficial.

The elution buffer can often contain one or more common buffer materials to maintain a desired pH. Examples are glycine, lysine, arginine, histidine, 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxy-propanesulfonic acid (MOPSO), N,N-bis-(hydroxyethyl)-2-aminoethanesulfonic acid (BES), 3-(N-morpholino)-propanesulfonic acid (MOPS), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-bis[2-hydroxyethyl]amino)-2-hydroxypropanesulfonic acid (DIPSO), N-(2-hydroxyethyl)piperazine-N'-(2-hydroxypropanesulfonic acid) (HEPPSO), 4-(2-hydroxyethyl)-1-piperazine propanesulfonic acid (EPPS), N-[tris(hydroxymethyl)-methyl]glycine (Tricine), N,N-bis(2-hydroxyethyl) glycine (Bicine), [(2-hydroxy-1,1-bis(hydroxymethyl)ethyl) amino]-1-propanesulfonic acid (TAPS), N-(1,1-dimethyl-2-hydroxyethyl)-3-amino-2-hydroxypropanesulfonic acid (AMPSO), tris(hydroxymethyl)amino¬ methane (Tris), and bis[2-hydroxyethyl]iminotris-[hydroxymethyl]methane (Bis-Tris). Other buffer materials known in the art may be used as well.

Resin restoration of an apatite-based in accordance with the descriptions herein can be performed after a single sample purification on the resin, or after a succession of purifications that collectively cause greater degradation the resin than a single purification. In certain implementations of the invention, a single resin is used for running a succession of samples on the resin with the restoration treatment performed after each sample. The number of samples run on the resin in such a procedure may be ten or more, and in many cases twenty or more and even fifty or more. Expressed in ranges, the number of samples (each followed by a restoration treatment) can be from ten to three hundred, from twenty to two hundred, or fifty to one hundred. Resin strength can be observed, for example, by uniaxial confined bulk compression.

In some cases, restoration treatment can be performed multiple times to achieve enhanced restoration of the apatite resin. For example, a degraded apatite resin may be restored by applying a solution of phosphate ion, a solution of calcium ion, and a solution of hydroxide ion, in succession and in order 2, 3, 4, or 5 times. Alternatively, a degraded apatite resin may be restored by applying a solution of calcium ion, a solution of phosphate ion, and a solution of hydroxide ion in succession and in order 2, 3, 4, or 5 times.

Target molecule purification, and chromatography in general, on an apatite-based resin is typically performed in a sequence of steps that are known in the art. Prior to equilibration and chromatography, the resin can be pre-equilibrated in a solution such as a salt and/or buffer solution, to displace a solution used for regenerating the resin, or a solution in which the resin is stored, or a solution of the restoration materials described above. The composition of the optimal pre-equilibration solution can vary with the composition of the solution that is being displaced and the composition of the target molecule, as well as the sample loading and elution solutions to be used in the purification. An appropriate pre-equilibration solution can thus include the same buffer or salt used for performing the chromatography, optionally at a higher concentration than that used in the chromatography. For example, if the solution used to perform chromatography comprises sodium phosphate at between about 0.5 mM and about 50 mM, pre-equilibration may occur in a solution comprising sodium phosphate at concentrations between about 0.2 M and about 0.5 M, more preferably in concentrations of sodium phosphate between about 0.3 M and about 0.4 M, inclusive.

Before the sample is applied to the column, the apatite-based resin is often equilibrated in the buffer or salt used to load the sample. Any of a variety of buffers or salts can be used, including those with cations such as sodium, potassium, ammonium, magnesium, and calcium, and anions such as chloride, fluoride, acetate, phosphate, and citrate. The pH of the equilibration solution is typically about 5.5 or higher, in many cases the pH is within the range of about 6.0 to about 8.6 or a range of about 6.5 to about 7.5. In some embodiments, equilibration may take place in a solution comprising a Tris or a sodium phosphate buffer. The sodium phosphate buffer may be present at a concentration between about 0.5 mM and about 50 mM, or between about 15 mM and 35 mM.

As noted above, all chromatographic, pre-treatment, and post-treatment steps described herein can be performed in a conventional chromatography column. The column can be run with or without pressure and from top to bottom or bottom to top, and the direction of the flow of fluid in the column can be reversed during the process. In some cases, it can be advantageous to reverse the flow of liquid while maintaining the packed configuration of the packed bed. The various steps may also be performed in a batch-wise manner in which the resin is first contacted with, then separated from, the solutions or liquids used to load the sample, wash the column, and elute the sample. Contacting and separation can be performed by any suitable means, including gravity, centrifugation, or filtration.

For protein separations, one example of a class of proteins are those produced by living host cells that have been genetically engineered to produce the protein. Methods of genetically engineering cells to produce proteins are well known in the art. See, e.g., Ausabel et al., eds. (1990), *Current Protocols in Molecular Biology* (Wiley, N.Y.). Such methods include introducing nucleic acids that encode and allow expression of the protein into living host cells. The host cells can be bacterial cells, fungal cells, or, preferably, animal cells grown in culture. Examples of bacterial host cells are *Escherichia coli* cells. Examples of suitable *E. coli* strains are HB101, DH5α, GM2929, JM109, KW251, NM538, and NM539. In some cases, an *E. coli* strain that fails to cleave foreign DNA can be used as a host cell. Examples of fungal host cells are *Saccharomyces cerevisiae, Pichia pastoris* and *Aspergillus* cells. Examples of animal cell lines are CHO, VERO, BHK, HeLa, Cos, MDCK, 293, 3T3, and WI38. New animal cell lines can be established using methods well known by those skilled in the art, such as by transformation, viral infection, and/or selection. In some cases, the separation can be performed on a protein secreted by the host cells. For example, the protein can be secreted into culture media and the culture media loaded onto the resin.

Further examples of proteins that can be purified in the apatite-based resins are recombinant fusion proteins comprising one or more constant antibody immunoglobulin domains, optionally an FC portion of an antibody, and a protein identical to or substantially similar to one of the following proteins: an flt3 ligand, a CD40 ligand, erythropoeitin, thrombopoeitin, calcitonin, Fas ligand, ligand for receptor activator of NF-kappa B (RANKL), tumor necrosis factor (TNF), TNF-related apoptosis-inducing ligand (TRAIL), thymic stroma-derived lymphopoietin, granulocyte colony stimulating factor, granulocyte-macrophage colony stimulating factor (GM-CSF), mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-$\beta$, leukemia inhibitory factor, oncostatin-M, and various ligands for cell surface molecules ELK and Hek (such as the ligands for eph-related kinases or LERKS).

Still further examples are recombinant fusion proteins containing one or more constant antibody immunoglobulin domains, optionally an FC portion of an antibody, plus a receptor for any of the above-mentioned proteins or proteins substantially similar to such receptors. These receptors include both forms of TNFR (referred to as p55 and p75), Interleukin-1 receptors types I and II, Interleukin-2 receptor, Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL (including TRAIL receptors 1, 2, 3, and 4), and receptors that comprise death domains, such as Fas or Apoptosis-Inducing Receptor (AIR).

Other examples of proteins are differentiation antigens (referred to as CD proteins) and their ligands, which are fused to at least one constant antibody immunoglobulin domain, optionally an FC portion of an antibody. Such antigens are disclosed in Leukocyte Typing VI (*Proceedings of the VIth International Workshop and Conference*, Kishimoto, Kikutani, et al., eds., Kobe, Japan, 1996). Examples of such antigens are CD27, CD30, CD39, CD40, and ligands thereto (CD27 ligand, CD30 ligand, etc.).

Still further examples are enzymatically active proteins and their ligands. Examples are recombinant fusion proteins comprising at least one constant antibody immunoglobulin domain plus all or part of one of the following proteins or their ligands or a protein substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

Still further examples are antibodies or portions thereof and chimeric antibodies, i.e., antibodies having at least one human constant antibody immunoglobulin domain coupled to one or more murine variable antibody immunoglobulin domains, or fragments thereof, and conjugates of an antibody and a cytotoxic or luminescent substance. Such substances include: maytansine derivatives (such as DM1); enterotoxins (such as a *Staphlyococcal* enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). Examples of antibodies or antibody/cytotoxin or antibody/luminophore conjugates are those that recognize any one or combination of the above-described proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1$\alpha$, IL-1$\beta$, IL4, IL-5, IL-8, IL-10, IL-2 receptor, IL-4 receptor, IL-6 receptor, IL-13 receptor, IL-18 receptor subunits, PDGF-$\beta$, VEGF, TGF, TGF-$\beta$2, TGF-$\beta$1, EGF receptor, VEGF receptor, C5 complement, IgE, tumor antigen CA125, tumor antigen MUCI, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF$\alpha$, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-$\gamma$-1 receptor, HLA-DR 10$\beta$, HLA-DR antigen, L-selectin, IFN-$\gamma$., Respiratory Syncitial Virus, human immunodeficiency virus (HIV), hepatitis B virus (HBV), *Streptococcus mutans,* or *Staphlycoccus aureus.*

EXAMPLE 1

Control Experiment

This example illustrates the deterioration of a hydroxyapatite resin over a series of cycles exposing the resin to conditions that simulate those encountered in protein separations (but without loading and eluting protein). The experiment was performed on a column measuring 20 cm in length and 2.2 cm in internal diameter, with an internal volume of 76 mL, and the packing was ceramic hydroxyapatite Type I in 40-micron particles weighing approximately 48 grams, the resulting mobile phase flow rate through the column being 250 cm/h. A series of 25 consecutive cycles were performed, each cycle consisting of the following eight steps:

TABLE I

Treatment Protocol for Simulated Cycles of Separation and Column Restoration

| Step | Mobile Phase | Column Volumes | Volume in mL | Time in minutes |
|---|---|---|---|---|
| 1 | Water | 1.0 | 76.0 | 4.8 |
| 2 | 400 mM NaPi, pH 7.0 | 3.0 | 228.1 | 14.4 |
| 3 | 10 mM NaPi, pH 6.8 | 6.0 | 456.2 | 28.8 |
| 4 | 10 mM NaPi, 1.0M NaCl, pH 6.5 | 6.0 | 456.2 | 28.8 |
| 5 | Water | 2.0 | 152.1 | 9.6 |
| 6 | 400 mM NaPi, pH 7.0 | 2.0 | 152.1 | 9.6 |
| 7 | Water | 1.0 | 76.0 | 4.8 |
| 8 | 1M NaOH | 2.0 | 152.1 | 9.6 |

In this protocol, Step 2 is a conditioning step to lower the pH of the column following the alkali treatment of Step 8; and Steps 3 and 4 expose the column to the conditions that are generally present during column equilibration, sample loading, and elution. Measurements of particle mass and particle strength (by uniaxial confined bulk compression, "UCBC") were taken before the first cycle and after the last cycle in each of three segments of the column—the top 25%, the middle 50%, and the bottom 25% (the mobile phase entry being at the top of the column). The results are listed in Table II below.

TABLE II

Changes in Solid Phase Mass and Strength at Three Column Locations for Simulated Cycles of Separation and Column Restoration

| Packing Location | Resin Mass | | | Particle Strength (UCBC @ 6.00 mm) | | |
|---|---|---|---|---|---|---|
| | Start | After 25 Cycles | Percent Change | N | psi | Percent Change |
| Top 25% | 12.00 g | 11.11 g | −7.42% | 136.9 | 516 | −49% |
| Middle 50% | 23.90 g | 22.26 g | −6.86% | 156.6 | 590 | −41% |
| Bottom 25% | 12.00 g | 11.23 g | −6.42% | 132.05 | 498 | −50% |
| Total | 47.90 g | 44.60 g | −6.89% | | | |
| | | | | Control: | 266.4 | 1003 |

The data in Table II indicate that the resin experienced chemical modification as evidenced by a loss of mass and a decline in particle strength. The overall mass loss was 6.89% and was approximately uniform throughout the height of the column. The decline in particle strength was greatest at the top and bottom, but generally extended throughout the column as well.

EXAMPLE 2

This example illustrates the result of including column restoration in accordance with the present invention in the column cycling of Example 1. A series of runs identical to those of Example I were performed on an identical hydroxyapatite column, except that a calcium chloride solution was passed through the column after the solutions that simulated the conditions for equilibration, sample loading, washing, and elution. Each cycle thus consisted of the following nine steps:

TABLE III

Treatment Protocol for Simulated Cycles of Separation and Column Restoration

| | | Amount | | |
|---|---|---|---|---|
| Step | Mobile Phase | Column Volumes | Volume in mL | Time in minutes |
| 1 | Water | 1.0 | 76.0 | 4.8 |
| 2 | 400 mM NaPi, pH 7.0 | 3.0 | 228.1 | 14.4 |
| 3 | 10 mM NaPi, pH 6.8 | 6.0 | 456.2 | 28.8 |
| 4 | 10 mM NaPi, 1.0M NaCl, pH 6.5 | 6.0 | 456.2 | 28.8 |
| 5 | 50 mM CaCl$_2$•2H$_2$O | 3.0 | 228.1 | 14.4 |
| 6 | Water | 2.0 | 152.1 | 9.6 |
| 7 | 400 mM NaPi, pH 7.0 | 2.0 | 152.1 | 9.6 |
| 8 | Water | 1.0 | 76.0 | 4.8 |
| 9 | 1M NaOH | 2.0 | 152.1 | 9.6 |

As in Example 1, 25 cycles were performed with measurements of particle mass and particle strength taken before the first cycle and after the last cycle. The measurements indicate that particle mass for the entire column increased by 4.72% and particle strength increased by 9%, over the course of the 25 cycles.

EXAMPLE 3

This example is a further illustration of column restoration in accordance with the present invention, illustrating the changes occurring in different parts of the same column to provide a direct comparison with the Control Example (Example 1). The column configuration was identical to that of the preceding examples, the treatment protocol was identical to that of Table III, and changes in mass and particle strength were obtained for each of three segments of the column before the first cycle and after the last cycle. The results are shown in Table IV below.

TABLE IV

Changes in Solid Phase Mass and Strength at Three Column Locations for Simulated Cycles of Separation and Column Restoration

| Packing Location | Resin Mass | | | Particle Strength (UCBC @ 6.00 mm) | | |
|---|---|---|---|---|---|---|
| | Start | After 25 Cycles | Percent Change | N | psi | Percent Change |
| Top 25% | 12.00 g | 11.89 g | −0.92% | 171.4 | 646 | −23% |
| Middle 50% | 23.90 g | 25.07 g | +4.90% | 209.3 | 789 | −6% |
| Bottom 25% | 12.00 g | 12.94 g | +7.83% | 251.4 | 947 | +13% |
| Total | 47.90 g | 49.90 g | +4.18% | | | |
| | | | | Control: | 222.4 | 838 |

Table IV shows that a slight loss in mass occurred in the upper 25% of the column while gains in mass occurred in the middle 50% and lower 25% of the column. The column as a whole increased in mass by 4.18%. Particle strength declined in the upper 25%, remained approximately neutral in the middle 50%, and increased by 13% in the lower 25%. Compare these results to those of Example 1 (Table II), where the mass change was a loss of 6.89%, and the particle strength declined in each of the three column segments, with a 50% decline in the lower 25%.

EXAMPLE 4

This example illustrates the effect of treating a column with a series of restoration treatments in accordance with the present invention but without the intervening treatments that simulate the conditions encountered during column equilibration, sample loading, washing, and elution. The column configuration was identical to those of the preceding examples, but each of the 25 cycles utilized the treatment protocol shown in Table V below.

TABLE V

Treatment Protocol for Column Restoration

| | | Amount | | |
|---|---|---|---|---|
| Step | Mobile Phase | Column Volumes | Volume in mL | Time in minutes |
| 1 | Water | 1.0 | 76.0 | 4.8 |
| 2 | 400 mM NaPi, pH 7.0 | 3.0 | 228.1 | 14.4 |
| 3 | Water | 6.0 | 456.2 | 28.8 |
| 4 | 50 mM CaCl$_2$•2H$_2$O | 6.0 | 456.2 | 28.8 |

Measurements of resin mass and particle strength were taken in three segments of the column as in Example 3, both before the first cycle and after the 25th cycle, and the results are shown in Table VI.

TABLE VI

Changes in Solid Phase Mass and Strength at Three Column Locations Over 25 Cycles of Column Restoration

| Packing Location | Resin Mass | | | Particle Strength (UCBC @ 6.00 mm) | | |
|---|---|---|---|---|---|---|
| | Start | After 25 Cycles | Percent Change | N | psi | Percent Change |
| Top 25% | 12.00 g | 11.75 g | −2.08% | 200.5 | 755 | −25% |
| Middle 50% | 23.90 g | 23.66 g | −1.00% | 277.5 | 1046 | +4% |
| Bottom 25% | 12.00 g | 11.90 g | −0.83% | 287.6 | 1084 | +8% |
| Total | 47.90 g | 47.31 g | −1.23% | | | |
| | | | | Control: | 266.3 | 1003 |

The small values of percent change in mass indicate that very little, if any, structural modification of the resin occurred. The 25% decrease in particle strength in the upper 25% of the column is characteristic of packed columns of apatite that have been used for repeated protein purifications without including calcium chloride in the equilibration, load, and elution solutions. The increase in the middle and lower sections show the positive effects of the calcium restoration material.

EXAMPLE 5

This example illustrates the effect of treating a column with a series of restoration treatments in accordance with the present invention after partial exposure to intervening treatments that simulate the conditions encountered during sample purification, except without exposure to alkali metal that would otherwise occur during elution or equilibration. The column configuration was identical to those of the preceding examples, but each of the 25 cycles utilized the treatment protocol shown in Table VII below.

TABLE VII

Treatment Protocol for Simulated Cycles of Separation and Column Restoration But Without Alkali Metal Halide Exposure

| | | Amount | | |
|---|---|---|---|---|
| Step | Mobile Phase | Column Volumes | Volume in mL | Time in minutes |
| 1 | Water | 2.0 | 76.0 | 9.6 |
| 2 | 50 mM CaCl$_2$·2H$_2$O | 3.0 | 228.1 | 14.4 |
| 3 | Water | 1.0 | 76.0 | 4.8 |
| 4 | 400 mM NaPi, pH 7.0 | 3.0 | 228.1 | 14.4 |
| 5 | 1M NaOH | 2.0 | 152.1 | 9.6 |
| 6 | Water | 1.0 | 152.1 | 4.8 |
| 7 | 400 mM NaPi, pH 7.0 | 2.0 | 152.1 | 9.6 |

Measurements of resin mass and particle strength were taken in three segments of the column as in Example 3, both before the first cycle and after the 25th cycle, and the results are shown in Table VIII.

TABLE VIII

Changes in Solid Phase Mass and Strength at Three Column Locations Over 25 Cycles of Column Restoration

| Packing Location | Resin Mass | | | Particle Strength (UCBC @ 6.00 mm) | | |
|---|---|---|---|---|---|---|
| | Start | After 25 Cycles | Percent Change | N | psi | Percent Change |
| Top 25% | 12.00 g | 11.77 g | −1.92% | 168.8 | 636 | −37% |
| Middle 50% | 23.90 g | 23.87 g | −0.13% | 263.6 | 993 | −1% |
| Bottom 25% | 12.00 g | 12.28 g | +2.33% | 235.4 | 887 | −12% |
| Total | 47.90 g | 47.92 g | +0.04% | | | |
| | | | | Control: | 266.3 | 1003 |

As in Example 4, the small values of percent change in mass indicated that very little, if any, structural modification of the resin occurred, and that a loss in particle strength occurred in the upper 25% of the column as is typical of packed columns of apatite that have been used for repeated protein purifications. The lesser losses in the middle and lower sections (and the increase in mass in the lower section) show the positive effects of the restoration protocol of the present invention.

EXAMPLE 6

This example illustrates a variation on the protocols of the preceding examples, by reversing the order of the calcium and phosphate ions. Otherwise, the treatment protocol for each of the 25 cycles was similar to those of Table III (Example 2) above. The column configuration was identical to those of the preceding examples and each cycle consisted of the following eleven steps:

TABLE IX

Treatment Protocol for Simulated Cycles of Separation and Column Restoration

| | | Amount | | |
|---|---|---|---|---|
| Step | Mobile Phase | Column Volumes | Volume in mL | Time in minutes |
| 1 | Water | 1.0 | 76.0 | 4.8 |
| 2 | 400 mM NaPi, pH 7.0 | 3.0 | 228.1 | 14.4 |
| 3 | 10 mM NaPi, pH 6.8 | 6.0 | 456.2 | 28.8 |
| 4 | 10 mM NaPi, 1.0M NaCl, pH 6.5 | 6.0 | 456.2 | 28.8 |
| 5 | Water | 1.0 | 76.0 | 4.8 |
| 6 | 400 mM NaPi, pH 7.0 | 2.0 | 152.1 | 9.6 |
| 7 | 10 mM NaPi, pH 6.8 | 0.5 | 38.0 | 2.4 |
| 8 | Water | 1.0 | 76.0 | 4.8 |
| 9 | 50 mM CaCl$_2$·2H$_2$O | 3.0 | 228.1 | 14.4 |
| 10 | Water | 2.0 | 152.1 | 9.6 |
| 11 | 1M NaOH | 2.0 | 152.1 | 9.6 |

Measurements of resin mass and particle strength were taken in three segments of the column as in Example 3, both before the first cycle and after the 25th cycle, and the results are shown in Table X.

TABLE X

Changes in Solid Phase Mass and Strength at Three Column Locations Over 25 Cycles of Column Restoration

| Packing Location | Resin Mass | | | Particle Strength (UCBC @ 6.00 mm) | | |
|---|---|---|---|---|---|---|
| | Start | After 25 Cycles | Percent Change | N | psi | Percent Change |
| Top 25% | 12.00 g | 10.98 g | −8.50% | 142.5 | 537 | −46% |
| Middle 50% | 23.90 g | 23.36 g | −2.26% | 179.1 | 675 | −33% |
| Bottom 25% | 12.00 g | 12.04 g | +0.33% | 209.2 | 788 | −21% |
| Total | 47.90 g | 46.38 g | −3.17% | | | |
| | | | | Control: | 266.3 | 1003 |

Both the mass and the particle strength declined over the course of the test, although not by as much as the control (Example 1, Table II). Nevertheless, comparison of these results with those of Example 3 (Table IV) show that improved resin restoration is achieved when the apatite surface that has been exposed to alkali metal salt elution (Step 4) is treated with calcium ion prior to treatment with phosphate ion.

EXAMPLE 7

This example illustrates the application of the restoration method of the present invention to a column to which a shallow phosphate gradient supplemented with NaCl has been applied. The column used in this example was 40 cm in length with an internal diameter of 1.6 cm and a flow rate of 200 cm/h or 6.70 mL/min. The packing material was the same as that used in the preceding examples, although the packing weight was 50.67 g and the column volume was 80.42 mL. A total of 25 cycles were run, and the protocol for each cycle was as shown in Table XI:

TABLE XI

Treatment Protocol for Simulated Cycles of Separation and Column Restoration with Phosphate Gradient

| | | Amount | | |
|---|---|---|---|---|
| Step | Mobile Phase | Column Volumes | Volume in mL | Time in minutes |
| 1 | 50 mM NaPi, 0.1M NaCl, pH 6.7 | 5.0 | 402.1 | 60.0 |
| 2 | 2 mM NaPi, 20 mM MES, 0.1M NaCl, pH 6.7 | 3.0 | 241.3 | 36.0 |
| 3 | 2 mM NaPi, 20 mM MES, 10 mM Tris, 0.1M NaCl, pH 6.7 | 7.0 | 563.0 | 84.0 |
| 4 | Water | 0.08 | 6.4 | 1.o |
| 5 | 20 mM NaPi, 0.1M NaCl, pH 6.7 | 3.0 | 241.3 | 36.0 |
| 6 | Gradient 8-90%: 2 mM NaPi, 0.1M NaCl, pH 6.7 → 50 mM NaPi, 0.1M NaCl, pH 6.7 | 10.0 | 804.2 | 120.0 |
| 7 | 50 mM NaPi, 0.1M NaCl, pH 6.7 | 2.0 | 160.8 | 24.0 |
| 8 | 50 mM CaCl$_2$•2H$_2$O | 3.0 | 241.3 | 36.0 |
| 9 | 2 mM NaPi, 0.1M NaCl, pH 6.7 | 0.1 | 8.0 | 1.2 |
| 10 | 400 mM NaPi, pH 7.0 | 2.0 | 160.8 | 24.0 |
| 11 | 1M NaOH | 2.0 | 160.8 | 24.0 |

Measurements of resin mass and particle strength are shown in Table XII.

TABLE XII

Phosphate Gradient Test: Changes in Solid Phase Mass and Strength at Three Column Locations Over 25 Cycles of Column Restoration

| Packing Location | Resin Mass | | | Particle Strength (UCBC @ 6.00 mm) | | |
|---|---|---|---|---|---|---|
| | Start | After 25 Cycles | Percent Change | N | psi | Percent Change |
| Top 25% | 15.02 g | 15.76 g | +4.93% | 206.0 | 776 | −23% |
| Middle 50% | 20.67 g | 23.33 g | +8.03% | 214.9 | 810 | −19% |
| Bottom 25% | 15.00 g | 16.24 g | +8.27% | 216.6 | 816 | −19% |
| Total | 50.69 g | 54.33 g | +7.18% | | | |
| | | | | Control: | 266.5 | 1004 |

While the particle strength values in Table XII show declines in all three sections of the column, a pilot-scale column packed to 40 cm in height and 20 cm in width was run through the same cycle without restoration steps 8 and 10 and without the intermediate wash step 9 (i.e., using cycles that instead consisted only of steps 1, 2, 3, 4, 5, 6, 7, and 11 of Table XI). The declines in particle strength for these curtailed cycles in the top, middle, and bottom sections of the column, were −26%, −40% and −46%, respectively, after only eleven cycles. A comparison between these values and those of Table XII shows that particle strengths in all three sections of the column declined to a much lesser degree (and over twice the number of cycles) when the restoration steps were included in each cycle than when the restoration steps were omitted.

In further tests, the protocol was repeated with the CaCl$_2$ concentration in Step 8 was reduced to 25 mM and 2 mM, respectively, all other steps being unchanged, to assess the effects of concentration on the packed resin. The results are shown in Table XIII, indicating some dependence on the concentration of CaCl$_2$ with the higher concentration providing a greater degree of restoration, particularly in the upper portions of the column.

TABLE XIII

Phosphate Gradient Test with Variable CaCl$_2$ Concentration: Changes in Solid Phase Mass and Strength at Three Column Locations Over 25 Cycles of Column Restoration

| Packing Location | Resin Mass | | | Particle Strength (UCBC @ 6.00 mm) | | |
|---|---|---|---|---|---|---|
| | Start | After 25 Cycles | Percent Change | N | Psi | Percent Change |
| Using 25 mM CaCl$_2$: | | | | | | |
| Top 25% | | 16.66 g | | 172.5 | 650 | −35% |
| Middle 50% | | 23.21 g | | 210.7 | 794 | −21% |
| Bottom 25% | | 13.41 g | | 198.85 | 749 | −25% |
| Total | 50.67 g | 53.28 | +5.15% | | | |
| Using 2 mM CaCl$_2$: | | | | | | |
| Top 25% | | 6.57 g | | 152.45 | 574 | −43% |
| Middle 50% | | 11.97 g | | 168.6 | 635 | −37% |
| Bottom 25% | | 5.49 g | | 194.85 | 734 | −27% |
| Total | 23.95 g | 24.03 g | +0.33% | | | |

Despite the loss in particle strength, the degree of loss shown in Table XIII at both concentrations is still significantly less than that observed in the comparison test cited above (i.e., the test using the protocol of Table XI minus steps 8, 9, and 10 for each cycle), at least in the middle and bottom sections of the column.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for increasing the resin mass and particle strength of an apatite-based chromatography resin after purification of a target molecule with said apatite-based chromatography resin, wherein said apatite-based chromatography resin is ceramic hydroxyapatite (CHT), said method comprising:
   (a) equilibrating said apatite-based chromatography resin;
   (b) after equilibrating said apatite-based chromatography resin, loading a sample containing a target analyte onto said apatite-based chromatography resin;
   (c) after loading said sample, eluting said target analyte from said apatite-based chromatography resin by passing a solution of elution buffer through said apatite-based chromatography resin; and
   (d) after eluting said target molecule, and before subsequent loading of additional target molecule:
      (i) passing a solution of calcium ion through said apatite-based chromatography resin;
      (ii) after (i), passing a solution of phosphate ion having a pH of at least about 6.5 through said apatite-based chromatography resin; and
      (iii) after (ii), passing a solution of hydroxide ion through said apatite- based chromatography resin;
   wherein (i), (ii), and (iii) are performed at concentrations of said calcium ions, phosphate ions, and hydroxide ions and at volumes of said solution of calcium ion, solution of phosphate ion, and solution of hydroxide ion that are effective to increase the resin mass and particle strength of said apatite-based chromatography resin.

2. The method of claim 1, further comprising passing an aqueous wash solution through said apatite-based chromatography resin after each of steps (i) and (ii).

3. The method of claim 1, wherein said solution of calcium ion has a calcium ion concentration of about 10 ppm to about 2000 ppm and is passed through said resin in an amount of about 1.0 resin volume to about 10.0 resin volumes.

4. The method of claim 1, wherein said solution of calcium ion has a calcium ion concentration of about 30 ppm to about 1000 ppm and is passed through said resin in an amount of about 1.5 resin volumes to about 6.0 resin volumes.

5. The method of claim 1, wherein said solution of phosphate ion has a pH of about 6.5 to about 9.0, has a phosphate ion concentration of about 50 mM to about 1 M, and is passed through said resin in an amount of about 1.0 resin volume to about 20.0 resin volumes.

6. The method of claim 1, wherein said solution of phosphate ion has a pH of about 6.5 to about 7.5, has a phosphate ion concentration of about 200 mM to about 750 mM, and is passed through said resin in an amount of about 1.5 resin volumes to about 10.0 resin volumes.

7. The method of claim 1, wherein said solution of hydroxide ion has a hydroxide ion concentration of about 0.1 M to about 5.0 M and is passed through said resin in an amount of about 1.0 resin volume to about 20.0 resin volumes.

8. The method of claim 1, wherein said solution of hydroxide ion has a hydroxide ion concentration of about 0.3 M to about 3.0 M and is passed through said resin in an amount of about 1.5 resin volume to about 10.0 resin volumes.

9. The method of claim 1, wherein said apatite-based chromatography resin is one that has been exposed to said elution buffer at a pH of about 8.0 or below.

10. The method of claim 1, wherein said apatite-based chromatography resin is one that has been exposed to said elution buffer at a pH of about 6.0 to about 8.0.

11. The method of claim 1, wherein said apatite-based chromatography resin is one that has been exposed to said elution buffer containing an alkali metal halide at a concentration of at least about 30 mM.

12. The method of claim 1, wherein said apatite-based chromatography resin is one that has been exposed to said elution buffer containing an alkali metal halide at a concentration of about 30 mM to about 3000 mM.

13. The method of claim 1, wherein said target molecule is a polypeptide.

14. In a method for purifying target molecules from a plurality of samples on an apatite-based chromatography resin by loading said samples in succession onto said resin and eluting said target molecules from said resin after each such loading with an elution buffer comprising an alkali metal salt, wherein said apatite-based chromatography resin is ceramic hydroxyapatite (CHT), the improvement comprising treating said resin after each target molecule elution and before subsequent sample loading by:
   (i) passing a solution of calcium ion through said resin;
   (ii) after (i), passing a solution of phosphate ion having a pH of at least about 6.5 through said resin; and
   (iii) after (ii), passing a solution of hydroxide ion through said resin;
   wherein steps (i), (ii), and (iii) are performed at concentrations of said ions and at volumes of said solution of calcium ion, solution of phosphate ion, and solution of hydroxide ion that are effective to increase resin mass and particle strength of said apatite-based chromatography resin.

15. The method of claim 14, wherein said plurality of samples consists of at least twenty samples.

16. The method of claim 14, wherein said plurality of samples consists of at least fifty samples.

17. The method of claim 14, further comprising passing an aqueous wash solution through said resin after each of steps (i), (ii), and (iii).

18. The method of claim 14, wherein said solution of calcium ion has a calcium ion concentration of about 10 ppm to about 2000 ppm and is passed through said resin in an amount of about 1.0 resin volume to about 10.0 resin volumes.

19. The method of claim 14, wherein said solution of calcium ion has a calcium ion concentration of about 30 ppm to about 1000 ppm and is passed through said resin in an amount of about 1.5 resin volumes to about 6.0 resin volumes.

20. The method of claim 14, wherein said solution of phosphate ion has a pH of about 6.5 to about 9.0, has a phosphate ion concentration of about 50 mM to about 1 M, and is passed through said resin in an amount of about 1.0 resin volume to about 20.0 resin volumes.

21. The method of claim 14, wherein said solution of phosphate ion has a pH of about 6.5 to about 7.5, has a phosphate ion concentration of about 200 mM to about 750 mM, and is passed through said resin in an amount of about 1.5 resin volumes to about 10.0 resin volumes.

22. The method of claim 14, wherein said solution of hydroxide ion has a hydroxide ion concentration of about 0.1 M to about 5.0 M and is passed through said resin in an amount of about 1.0 resin volume to about 20.0 resin volumes.

23. The method of claim 14, wherein said solution of hydroxide ion has a hydroxide ion concentration of about 0.3 M to about 3.0 M and is passed through said resin in an amount of about 1.5 resin volume to about 10.0 resin volumes.

24. The method of claim 14, wherein said elution buffer has a pH of about 8.0 or below.

25. The method of claim 14, wherein said elution buffer has a pH of about 6.0 to about 8.0.

\* \* \* \* \*